United States Patent [19]

Akahane et al.

[11] Patent Number: 4,775,592

[45] Date of Patent: Oct. 4, 1988

[54] FLUOROALUMINOSILICATE GLASS POWDER FOR DENTAL GLASS IONOMER CEMENT

[75] Inventors: Shoji Akahane, Higashikurume; Kazuo Hirota, Tokyo; Kentaro Tomioka, Chofu, all of Japan

[73] Assignee: G-C Dental Industrial Corp., Tokyo, Japan

[21] Appl. No.: 898,947

[22] Filed: Aug. 21, 1986

[30] Foreign Application Priority Data

Sep. 29, 1985 [JP] Japan ................................ 60-206299

[51] Int. Cl.$^4$ .................... A32B 5/16; C03C 3/076; C03C 3/062; A61K 5/01
[52] U.S. Cl. .................................... 428/406; 428/404; 106/35; 433/226; 433/228.1; 523/116; 501/55; 501/63; 501/68; 501/73; 501/57; 501/66; 501/11; 501/18; 427/126.2; 427/217; 427/219; 427/389.7; 427/83.5
[58] Field of Search .............. 106/35; 433/199, 226, 433/228.1; 501/55, 73, 53, 63, 68, 64, 57, 66, 11, 15, 17, 18; 428/404, 406; 523/116; 427/126.1, 126.2, 215, 217, 219, 314, 383.5, 389.7, 397.7, 397.8

[56] References Cited

U.S. PATENT DOCUMENTS

| | | | |
|---|---|---|---|
| 3,814,717 | 6/1974 | Wilson et al. | 524/443 |
| 4,143,018 | 3/1979 | Crisp et al. | 501/57 |
| 4,342,677 | 8/1982 | Muramatsu et al. | 523/116 |
| 4,447,550 | 5/1984 | Leroy et al. | 501/75 |

Primary Examiner—Josephine Barr
Attorney, Agent, or Firm—Oblon, Fisher, Spivak, McClelland & Maier

[57] ABSTRACT

A fluoroaluminosilicate glass powder for dental glass ionomer cement, a surface of which is treated with a fluoride in an amount of from 0.01 to 5 parts by weight based on 100 parts by weight of the glass powder, is disclosed. The fluoroaluminosilicate glass powder of the invention is improved in not only physical properties such as crushing strength but also mixing workability without impairing the inherent characteristics thereof for the dental use.

7 Claims, No Drawings

FLUOROALUMINOSILICATE GLASS POWDER FOR DENTAL GLASS IONOMER CEMENT

FIELD OF THE INVENTION

The present invention relates to a glass powder used for dental glass ionomer cement and more particularly, to a fluoroaluminosilicate glass powder used for dental glass ionomer cement, a surface of which is treated with a fluoride in an amount of from 0.01 to 5 parts by weight based on 100 parts by weight.

BACKGROUND OF THE INVENTION

A glass ionomer cement which is used mainly in the dentistry is prepared by setting a fluoroaluminosilicate glass powder and a polycarboxylic acid such as polyacrylic acid in the presence of water, and a set body thereof has transparency and is aesthetically excellent. Further, it has no irritant action to a dental pulp and excellent biocompatibility. Still further, it exhibits an excellent adhesion to any of enamel and dentin tooth substances, is good in marginal sealing, and can maintain durability in the mouth over a long period of time. Even further, since the glass powder contains fluorine, one can expect that it has a tooth substance-strengthening function. In view of these characteristics, the dental glass ionomer cement is widely used in various applications such as restoration and filling of dental cavity, cementing of prosthesis and orthodontic band, lining of dental cavity, core construction, pit and fissure sealant.

However, with respect to this glass ionomer cement, when a polyacrylic acid aqueous solution and a fluoroaluminosilicate glass powder are merely combined and mixed, the mixed material is low in fluidity and is poor in workability. Further, it requires a long period of time for setting, and a surface thereof is broken by the contact with saliva, whereby not only the surface of the cement becomes weak but also its final strength is not satisfactory.

In order to overcome these defects, a number of methods have been investigated. For example, Japanese Laid-Open Patent No. 101893/1977 discloses a method by which the above-described defects are solved and the characteristics of the glass ionomer cement are exhibited, i.e., it discloses a setting liquid comprising a 45–60% aqueous solution of polyacrylic acid or an acrylic acid copolymer having incorporated therein to from 7 to 25%, based on the total weight, of one or more of a polybasic carboxylic acid. Further, the present applicant disclosed in Japanese Laid-Open Patent No. 2210/1982 a dental glass ionomer cement setting liquid comprising a 45–55% aqueous solution of an acrylic acid/maleic acid copolymer having incorporated therein to from 10 to 25% of tartaric acid and from 0.1 to 5% of at least one fluorocomplex salt, based on the total weight. Still further, various other attempts have been made. In accordance with these methods, not only physical properties but also workability and water resistance are improved.

While various improvements of the dental glass ionomer cement have been investigated, the fluidity of the mixed paste is still insufficient as compared with that of a zinc phosphate cement which has hitherto been widely used and, therefore, it cannot yet be said that the workability is in an ideal state. In particular, when the glass ionomer cement is used for cementing of prosthesis, the flow is so poor that the cement film is likely to thicken and, hence, there was often found no fitting of the prosthesis. That is, at the time when the manipulation can be performed immediately after the mixing, it is necessary to increase the fluidity of the cement without lowering the physical properties. Further, when the glass ionomer cement is used for the filling, since it is inferior in physical properties such as crushing strength as compared with dental amalgams or dental composite resins, a glass ionomer cement which will be further improved in crushing strength is needed depending upon symptoms.

SUMMARY OF THE INVENTION

In order to overcome the above-described defects, the present inventors have made extensive investigations regarding a glass powder which is used for the dental glass ionomer cement and have astonishingly found that when a surface of a fluoroaluminosilicate glass powder is treated with a fluoride in an amount of from 0.01 to 5 parts by weight based on 100 parts by weight of the glass powder, not only its physical properties such as crushing strength are improved, but also the fluidity of a mixed cement is increased to improve the workability, which findings led to the present invention.

That is, an object of the present invention is to provide a fluoroaluminosilicate glass powder for dental glass ionomer cement, a surface of which is treated with a fluoride in an amount of from 0.01 to 5 parts by weight based on 100 parts by weight of the glass powder.

DETAILED DESCRIPTION OF THE INVENTION

A dental glass ionomer cement using a fluoroaluminosilicate glass powder, a surface of which is treated with a fluoride, is increased in fluidity of a cement paste immediately after the mixing and improved in the manipulation for mixing. Therefore, in the case that it is used for cementing of prosthesis, there is an effect that the film of the cement does not become readily thick. Further, a time required for cement workability until the initial setting in which the fluidity of the cement surface completely disappears is shortened, and the setting proceeds sharply. That is, it is possible to prolong the working time while the initial setting time remaining the same. Still further, a dental glass ionomer cement using a glass powder treated with a fluoride is improved in physical properties such as crushing strength.

As the fluoroaluminosilicate glass powder used in the present invention, a powder which is prepared by melting, as main components, silica ($SiO_2$) and alumina ($Al_2O_3$) together with, as a melting agent, a fluoride or a phosphate at high temperatures of 1000° C. or higher, followed by cooling and grinding can be used. Any fluoroaluminosilicate glass powder which reacts with a polycarboxylic acid in the presence of water can be used in the present invention. However, in general, those fluoroaluminosilicate glass powders which are prepared by melting a mixed component containing from 25 to 50% of silica, from 15 to 40% of alumina, from 10 to 40% of a fluoride, and from 0 to 20% of a phosphate at high temperatures of 1000° C. or higher, followed by cooling and grinding are preferably used. Further, with respect to the silica and alumina, it is only required that they are present in equivalent amounts as raw materials for glass, and any other materials which can be expected to have a similar function in the glass are employable. For example, it is possible to replace part or the whole of silica or alumina by aluminum silicate, silica gel, aluminum hydroxide, etc. if the equivalent amount is ensured. For example, if aluminum hydroxide is used as a raw material in place of alumina, there is a merit that the melting can be readily performed. In this case, the proportion of the aluminum hydroxide as calculated in terms of the alumina content may be determined. Examples of the fluoride which is used as one of the raw materials of glass include not only fluorides of zinc, aluminum, yttrium, lanthanum, zirconium, etc. in addition to those of alkali metals and alkaline earth metals but also fluorocomplex salts such as sodium hexafluoroaluminate ($Na_3AlF_6$) and potassium hexafluoroaluminate ($K_3AlF_6$). Examples of the phosphate which is also used as one of the raw materials for glass include phosphates of alkali metals, alkaline earth metals, zinc, aluminum, yttrium, lanthanum, zirconium, etc. The phosphate is not particularly restricted to an orthophosphate, but various other phosphates such as pyrophosphates, monobasic phosphates, and dibasic phosphates can be widely used.

The fluoroaluminosilicate glass powder can properly contain, as raw materials, oxides, carbonates, hydroxides, etc. For example, oxides, carbonates, and hydroxides of alkaline earth metals, yttrium, lanthanum, zinc, zirconium, titanium, etc. can be added as the raw materials for the use.

As the fluoroaluminosilicate glass powder prepared by melting and grinding the above-described raw materials, a powder which passes through an #80 sieve is preferred, and a powder which passes through a #150 sieve is particularly preferred. Further, in the case that the powder is restrictedly prepared for the use of cementing, a maximum diameter thereof is preferably of 25 μm or less.

The fluoride which is used for the surface treatment of the fluoroaluminosilicate glass powder is not particularly restricted, but in general, metal fluorides are preferred. Examples of the metal fluoride which can be used include aluminum fluoride, zinc fluoride, tin fluoride, zirconium fluoride, acidic sodium fluoride, acidic potassium fluoride, and various fluorocomplex salts. Among them, the fluorocomplex salts disclosed in Japanese Laid-Open Patent No. 2210/1982 by the present applicant are especially preferred.

The fluoro complex salts effectively used in the present invention include, for instance, potassium tetrafluoroberyllate, ammonium tetrafluoroberyllate, sodium hexafluorozirconate, potassium hexafluorozirconate, potassium heptafluoroniobate, potassium heptafluorotantalate, sodium hexafluorosilicate, potassium hexafluorosilicate, lithium hexafluorosilicate, ammonium hexafluorosilicate, iron hexafluorosilicate, nickel hexafluorosilicate, zinc hexafluorosilicate, tin hexafluorosilicate, magnesium hexafluorosilicate, manganese hexafluorosilicate, sodium hexafluorotitanate, potassium hexafluorotitanate, ammonium hexafluorotitanate, nickel hexafluorotitanate, potassium tetrafluoroborate, ammonium tetrafluoroborate, manganese tetrafluoroborate, iron tetrafluoroborate, nickel tetrafluoroborate, tin tetrafluoroborate, indium tetrafluoroborate, zinc tetrafluoroborate, antimony tetrafluoroborate, and boron triflouride-acetate complex. Most preferable are potassium tetrafluoroberyllate, sodium hexafluorozirconate, potassium hexafluorozirconate, sodium hexafluorosilicate, potassium hexafluorosilicate, zinc hexafluorosilicate, magnesium hexafluorosilicate, sodium hexafluorotitanate, potassium hexafluorotitanate, and ammonium hexafluorotitanate.

Even when these fluoride and fluoroaluminosilicate glass powder are simply mixed and dispersed, neither the fluidity of the cement paste immediately after the mixing is increased nor an improvement in workability is achieved. Such effects are realized first by the treatment of a surface of the glass powder with a fluoride. It is quite important from the clinical standpoint that the fluidity is improved. That is, first of all, the working time of the cement is increased without delay of the initial setting time. The glass ionomer cement is generally supplied in the form of a powder and liquid to clinicians. Depending upon the product, there may be a form that a liquid component is powdered and then added to a powder component, followed by mixing with water. In any of the cases, when a dentist actually uses the cement, since the cement is used upon mixing, it is required that the cement has as much allowance for as possible, whereas it rapidly sets as fast as possible at the stage when the working has been completed. Accordingly, the setting characteristic greatly influences the clinical practice. This setting characteristic is greatly improved by the surface treatment of the glass powder with a fluoride. Secondly, since the fluidity of the mixed cement is increased, the mixing is readily performed, i.e., the mixing workability is improved. Thus, it can be expected to minimize difference in the individuals who perform the mixing. Thirdly, in the case that the glass ionomer cement is used for cementing of prosthesis or orthodontic band, the cement layer thereof can be made thin. This means that in the case that the glass ionomer cement is present between a prosthesis and a tooth, not only the adhesion of a prosthesis to a tooth substance is improved, but also the durability can be improved.

Further, the above-described treatment increases the strength of a hardened cement. The increase in the strength can be effected by merely mixing the glass powder with the fluoride. However, the strength is further increased by the surface treatment. This is considered to be caused from that, since a setting reaction of the cement is assumed to take place on the glass powder surface, its effect is large rather in the surface-treated glass powder. The fluidity of the mixed cement can be specifically investigated by, for example, a consistency measurement method as described below. That is, the consistency measurement method is a method in which 0.5 ml of the mixed cement paste is measured and placed on a glass plate, and one minute after the start of the mixing, another glass plate is placed on the cement paste together with a load, to thereby measure the spread of the cement.

One example in which a difference in consistency between the cement powder added by the fluoride and the cement powder treated with the fluoride was specifically measured is given below.

A fluoroaluminosilicate glass powder prepared by melting a raw material containing 40% of silica sand, 26% of alumina, 20% of fluorite, 5% of aluminum fluoride, 2% of sodium fluoride, and 7% of calcium phosphate and then grinding the mixture was mixed with a glass ionomer cement setting liquid (Fuji Ionomer Type I, G-C Dental Industrial Corp.) in a ratio of powder to liquid of 1.5/1.0, and the consistency was found to be 22 mm. When to this mixture was added a fluoride (potassium hexafluorotitanate) in an amount of 1% of the glass powder and simply mixed, the consistency was found to be 21 mm. On the other hand, when the glass powder was treated with the same amount of the fluoride, the consistency was found to be 30 mm. In order to examine to what extent the difference in fluidity influences the performance as an actual dental cement, the initial setting time, film thickness, and crushing strength were measured in accordance with JIS T6602 as defined for a dental zinc phosphate cement. Further, the fluidity of the cement paste was evaluated using the point of a spatula, to thereby determine the working time. The results obtained are summarized in the following table:

|  | Powder State | | |
| --- | --- | --- | --- |
|  | No addition/ No Treatment | Addition with 1% Fluoride | Surface Treatment with 1% Fluoride |
| Working Time | 2'10" | 2'05" | 2"55" |
| Initial Setting Time | 5'45" | 5'30" | 5'30" |
| Film Thickness ($\mu$m) | 28 | 28 | 20 |
| Crushing Strength (kg/cm$^2$) | 1480 | 1570 | 1710 |

These effects are not limited to the above-specified example with respect to the glass powder formulation but are generally observed with respect to a fluoroaluminosilicate glass powder. In particular, in the present invention, the effects are remarkable with respect to a fluoroaluminosilicate glass powder obtained from the above-described raw material containing from 20 to 50% of silica, from 10 to 40% of alumina, from 10 to 50% of a fluoride, and from 0 to 20% of a phosphate. As the treatment method to be employed, any conventional treatment methods are properly chosen and employed. The typical examples include a method in which the fluoride is dissolved in distilled water or an aqueous solution of an acid and mixed with the glass powder, follwed by heating to evaporate off the water content; and a method in which the glass powder and the fluoride are well mixed and simply heated.

The glass ionomer cement is prepared by setting the fluoroaluminosilicate glass powder and polycarboxylic acid in the presence of water, and it is confirmed that a considerable amount of fluorine in the glass powder is transferred into a tooth substance. This means that a dental caries-preventing effect can be expected because the fluorine has a tooth substance-strengthening function.

As the polycarboxylic acid which sets the fluoroaluminosilicate glass powder treated with a fluoride according to the present invention, polymer acids known to be used for the glass ionomer cement can be used. The examples include polyacrylic acid, acrylic acid/itaconic acid copolymer, and acrylic acid/maleic acid copolymer. These polymer acids are used in the form of either a powder or an aqueous solution. In the case that the polymer acid is used in the form of a powder, it is mixed with the fluoroaluminosilicate glass powder treated with a fluoride according to the present invention. In this case, when it is actually used in the clinical application, it is necessary to add water to set the cement.

On the other hand, in the case that the polymer acid is used in the form of an aqueous solution, an aqueous solution of the polymer acid is merely mixed with the glass powder of the present invention. Further, it is also possible that a part of the polymer acid is in the form of an aqueous solution, whereas the remainder is in the form of a powder, to mix with the cement.

In any of the above-described cases, improvers known to be used for the glass ionomer cement can be used. Examples of the improver include the polybasic carboxylic acids as disclosed in Japanese Laid-Open Patent No. 101893/1977.

The present invention is explained below in more detail with reference to the following Examples and Comparative Examples, but it is not to be construed that the invention is limited thereto.

EXAMPLE 1

100 g of a powder of a commercially available glass ionomer cement (for cementing, "Fuji Ionomer Type I", G-C Dental Industrial Corp.) and 50 g of a 1% aqueous solution of potassium hexafluorotitanate were well mixed using a mortar. In order to completely evaporate off the water content for drying, the mixture was placed in an electric furnace set up at 95° C. and allowed to stand therein for one hour. Thereafter, the temperature was elevated to 120° C., and the drying was carried out for additional 2 hours.

The thus obtained powder was mixed with a setting liquid of a commercially available glass ionomer cement (for cementing, "Fuji Ionomer Type I", G-C Dental Industrial Corp.) in a proportion of 1.4 g of the former per gram of the latter, and the initial setting time, crushing strength (after one day), and film thickness (1.5 minutes after the start of the mixing) of the mixture were measured in a thermostat at a temperature of 23.0°±0.2° C. and a humidity of 50±2% according to JIS T6602 as defined for a zinc phosphate cement. Further, the fluidity was evaluated using the point of a spatula, to thereby determine the working time. As the result of the measurement, the initial setting time, working time, film thickness, and crushing strength were 5 minutes and 20 seconds, 2 minutes and 50 seconds, 20 $\mu$m, and 1720 kg/cm$^2$, respectively.

COMPARATIVE EXAMPLE 1

The physical properties of a commercially available glass ionomer cement (for cementing, "Fuji Tonomer Type I", G-C Dental Industrial Corp.) were examined in the same manner as in Example 1.

As a result, the initial setting time, working time, film thickness, and crushing strength were 5 minutes and 30 seconds, 2 minutes and 00 second, 25 $\mu$m, and 1420 kg/cm$^2$, respectively.

EXAMPLE 2

42 g of silica sand, 26 g of alumina, 20 g of fluorite, 10 g of cryolite, and 2 g of calcium phosphate were mixed in a mortar, and the mixture was charged into a platinum crucible and melted at 1250° C. for 4 hours. After the melting, the resulting mixture was cooled and then ground by means of a ball mill for 10 hours, from which a powder passing through a #150 sieve was prepared as a fluoroaluminosilicate glass powder. Separately, a 0.5% aqueous solution of zinc fluoride was prepared, and 100 parts by weight of the 0.5% aqueous solution of zinc fluoride was well mixed with 100 parts by weight of the glass powder, and the mixture was dried at 95° C. for one hour and further at 120° C. for 2 hours. The dried powder was sieved with a #150 sieve to prepare a sample.

The thus prepared sample powder was mixed with a commercially available dental glass ionomer cement setting liquid (for cementing, "Fugi Ionomer Type I", G-C Dental Industrial Corp.) in a proportion of 1.4 g of the former per gram of the latter. Thereafter, the physical properties were examined in the same manner as in Example 1.

As a result, the initial setting time, working time, film thickness, and crushing strength were 5 minutes and 30 seconds, 2 minutes and 20 seconds, 21 μm, and 1650±70 kg/cm$^2$, respectively.

EXAMPLE 3

The fluoroaluminosilicate glass powder as prepared in Example 2 was treated with a 0.5% aluminum fluoride aqueous solution which had been previously prepared. That is, 100 parts by weight of the glass powder and 200 parts by weight of the 0.5% aluminum fluoride aqueous solution were well mixed in a mortar, and the mixture was dried at 95° C. for 2 hours and further at 120° C. for 2 hours. After drying, the powder was passed through a #150 sieve to prepare a sample. 80 g of the thus prepared sample was mixed with 20 g of a polyacrylic acid powder using a mortar to prepare a cement powder.

Separately, a 15% tartaric acid aqueous solution was prepared as a setting liquid. The cement powder and the liquid were mixed in a proportion of 2.0 g of the former per gram of the latter. Thereafter, the physical properties were examined in the same manner as in Example 1.

As a result, the initial setting time, working time, film thickness, and crushing strength were 5 minutes and 15 seconds, 2 minutes and 50 seconds, 21 μm, and 1630±110 kg/cm$^2$, respectively.

EXAMPLE 4

The fluoroaluminosilicate glass as melted in Example 2 was ground for 5 hours by means of a ball mill, passed through a #150 sieve, and then ground for an additional 5 hours to prepare a glass powder. Separately, a 1% zirconium potassium fluoride aqueous solution was prepared. 100 parts by weight of the glass powder and 200 parts by weight of the 1% zirconium potassium fluoride aqueous solution were mixed, and the mixture was dried at 95° C. for 2 hours and further at 120° C. for 2 hours. After the drying, the dried powder was passed through a #150 sieve to prepare a sample. 75 g of the thus prepared sample was mixed with 25 g of a polyacrylic acid copolymer powder to prepare a cement powder.

Separately, a 20% tartaric acid aqueous solution was prepared as a setting liquid. The cement powder and the liquid were mixed in a proportion of 2.0 g of the former per gram of the latter. Thereafter, the physical properties were examined in the same manner as in Example 1.

As a result, the initial setting time, working time, film thickness, and crushing strength were 5 minutes and 00 seconds, 2 minutes and 50 seconds, 18 μm, and 1700±90 kg/cm$^2$, respectively.

EXAMPLES 5 to 7

A 2% sodium hexafluorotitanate aqueous solution was prepared as a liquid for treating the fluoroaluminosilicate glass powder as prepared in Example 4. That is, 100 parts by weight of the glass powder was treated with the 2% sodium hexafluorotitanate aqueous solution in an amount of 20 parts by weight, 50 parts by weight, and 100 parts by weight, respectively. Each of the mixtures was dried at 95° C. for one hour and further at 120° C. for 2 hours. After the drying, the dried powder was passed through a #150 sieve to prepare a cement powder.

Separately, a setting liquid consisting of 40% of an acrylic acid/maleic acid copolymer (a monomer ratio: 85/15), 14.5% of tartaric acid, 45% of distilled water, and 0.5% of sodium titanium fluoride was prepared as a cement liquid.

Each of the cement powders was mixed with the setting liquid in a proportion of 1.5 g of the former per gram of the latter. The physical properties were examined in the same manner as in Example 1. The results obtained are shown in Table 1:

TABLE 1

| Example No. | A | B | C | D | E |
|---|---|---|---|---|---|
| 5 | 20 | 5'15" | 2'50" | 20 | 1740 ± 80 |
| 6 | 50 | 5'15" | 3'00" | 20 | 1750 ± 90 |
| 7 | 100 | 5'00" | 3'00" | 19 | 1780 ± 100 |

A: proportion of 2% Na$_2$TiF$_6$ aqueous solution per 100 parts by weight of glass
B: initial setting time
C: working time
D: film thickness (μm)
E: crushing strength (kg/cm$^2$)

COMPARATIVE EXAMPLE 2

A glass powder as prepared in the same manner as in Example 2 except that the 0.5% aqueous solution of zinc fluoride was not used was mixed with the same setting liquid as in Example 2, followed by examining the physical properties.

As a result, the initial setting time, working time, film thickness, and crushing strength were 6 minutes and 00 second, 1 minute and 50 seconds, 26 μm, and 1400±90 kg/cm$^2$, respectively.

COMPARATIVE EXAMPLE 3

In Example 3, 100 parts by weight of the fluoroaluminosilicate glass powder was simply mixed with 1 part by weight of aluminum fluoride to prepare a sample. 80 g of the thus prepared sample was mixed with 20 g of a polyacrylic acid powder in a mortar to prepare a cement powder.

Separately, a 15% tartaric acid aqueous solution was prepared as a setting liquid in the same manner as in Example 3. The cement powder and the setting liquid were mixed in a proportion of 2.0 g of the former per gram of the latter. Thereafter, the physical properties were examined in the same manner as in Example 3.

As a result, the initial setting time, working time, film thickness, and crushing strength were 5 minutes and 45 seconds, 2 minutes and 00 second, 25 μm, and 1600±60 kg/cm$^2$, respectively.

EXAMPLE 8 AND COMPARATIVE EXAMPLE 4

In each of Example 3 and Comparative Example 3, the proportion of the cement powder to the liquid was changed to one for the filling consistency, i.e., 3.2 g of the former per gram of the latter, and the initial setting time, crushing strength, and working time were measured in the same manner. The results obtained are shown in Table 2:

TABLE 2

|  | Initial Setting Time | Working Time | Crushing Strength (kg/cm$^2$) |
|---|---|---|---|
| Example 8 | 4'15" | 2'10" | 2150 ± 140 |

TABLE 2-continued

|  | Initial Setting Time | Working Time | Crushing Strength (kg/cm$^2$) |
|---|---|---|---|
| Comparative Example 4 | 4'30" | 1'30" | 1900 ± 120 |

It is evidnet from the foregoing results that the cements as prepared in Examples 1 to 7 have remarkably excellent properties as a dental cement as compared with those prepared in Comparative Examples 1 to 3, i.e., in Examples 1 to 7, the working time is prolonged and the crushing strength is increased. Further, the thick paste cement for use of filling as prepared in Example 8 is excellent in crushing strength and working time as compared with the cement paste as prepared in Comparative Example 4, which has a similar fluidity of the cement, and, therefore, the former is also an excellent dental cement.

While the invention has been described in detial and with reference to specific embodiments thereof, it will be apparent to one skilled in the art that various changes and modification can be made therein without departing from the spirit and scope thereof.

What is claimed is:

1. A fluoroaluminosilicate glass powder suitable as a dental glass ionomer cement, which is produced by treating the surface of a fluoroaluminosilicate glass powder with a metal fluoride or fluorocomplex salt in an amount of from about 0.01 to 5 parts by weight of said metal fluoride or fluorocomplex salt based on 100 parts by weight of the glass powder; and wherein said fluoroaluminosilicate glass powder comprises 25 to 50 weight percent of silica, 15 to 40 weight percent of alumina, 10 to 40 weight percent of fluoride and 0 to 20% of a phosphate; and wherein said metal fluoride is selected from the group consisting of a fluoride of zinc, aluminum, tin, zirconium acidic sodium; and said fluorocomplex salt is selected from the group consisting of potassium tetrafluoroberyllate, ammonium tetrafluoroberyllate, sodium hexafluorozirconate, potassium hexafluorozirconate, potassium heptafluoroniobate, potassium heptafluorotantalate, sodium hexafluorosilicate, potassium heptafluorosilicate, lithium hexafluorosilicate, ammonium hexafluorosilicate, iron hexafluorosilicate, nickel hexafluorosilicate, zinc hexafluorosilicate, tin hexafluorosilicate, magnesium hexafluorosilicate, sodium hexafluorotitanate, potassium hexafluorotitanate, ammonium hexafluorotitanate, nickel hexafluorotitanate, potassium tetrafluoroborate, ammonium tetrafluoroborate, manganese tetrafluoroborate, iron tetrafluoroborate, nickel tetrafluoroborate, tin tetrafluoroborate, indium tetrafluoroborate, zinc tetrafluoroborate, antimony tetrafluoroborate, and boron trifluoride-acetate complex.

2. The fluoroaluminosilicate glass powder as claimed in claim 1, wherein said glass powder is capable of passing through a number 80 sieve.

3. The fluoroaluminosilicate glass powder as claimed in claim 2, wherein said glass powder is capable of passing through a number 150 sieve.

4. The fluoroaluminosilicate glass powder of claim 1, wherein said fluoroaluminosilicate glass having the surface thereof treated with a metal fluoride or fluorocomplex salt is prepared by melting a composition containing from 25 to 50 weight percent of said silica, from 15 to 40 weight percent of said alumina, from 10 to 40 weight percent of said fluoride, and from 0 to 20 percent by weight of said phosphate at a temperature of 1,000° C. or higher, followed by cooling and grinding.

5. The fluoroaluminosilicate glass powder as claimed in claim 1, wherein said phosphate is an orthophosphate, a pyrophosphate, or a monobasic or dibasic phosphate.

6. The fluoroaluminosilicate glass powder as claimed in claim 1, wherein said phosphate is selected from the group consisting of a phosphate of an alkali metal, an alkaline earth metal, zinc, aluminum, yttrium, lanthanum and zirconium.

7. The fluoroaluminosilicate glass powder as claimed in claim 1, wherein said glass powder consists essentially of particles having a maximum diameter of 25 μm or less.

* * * * *